(12) United States Patent
Bjernulf

(10) Patent No.: US 7,153,404 B2
(45) Date of Patent: Dec. 26, 2006

(54) GEL SPOT PICKER

(75) Inventor: Olle Bjernulf, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 597 days.

(21) Appl. No.: 10/275,371

(22) PCT Filed: May 11, 2001

(86) PCT No.: PCT/EP01/05425

§ 371 (c)(1),
(2), (4) Date: Mar. 3, 2003

(87) PCT Pub. No.: WO01/86278

PCT Pub. Date: Nov. 15, 2001

(65) Prior Publication Data

US 2003/0183523 A1    Oct. 2, 2003

(30) Foreign Application Priority Data

May 12, 2000 (SE) .................................. 0001778
Jun. 13, 2000 (SE) .................................. 0002041

(51) Int. Cl.
*G01N 27/447* (2006.01)
*G01N 27/453* (2006.01)

(52) U.S. Cl. .................. 204/462; 204/463; 204/613

(58) Field of Classification Search ............... 204/462, 204/463, 456, 606, 613, 616
See application file for complete search history.

(56) References Cited

U.S. PATENT DOCUMENTS

| 4,111,784 A | * | 9/1978 | Dahms ..................... 204/617 |
| 5,073,963 A | | 12/1991 | Sammons et al. |
| 5,627,022 A | * | 5/1997 | Renfrew et al. ............... 435/4 |
| 5,993,627 A | * | 11/1999 | Anderson et al. ............ 204/456 |
| 6,342,143 B1 | * | 1/2002 | Minden ..................... 204/462 |
| 6,521,111 B1 | * | 2/2003 | Amshey et al. ............ 204/616 |
| 6,554,991 B1 | * | 4/2003 | Goodman et al. .......... 204/613 |

FOREIGN PATENT DOCUMENTS

| WO | WO 94/20844 | 9/1994 |
| WO | WO 98/23950 | 6/1998 |
| WO | WO 00/49397 | 8/2000 |

* cited by examiner

*Primary Examiner*—Kaj K. Olsen
(74) *Attorney, Agent, or Firm*—Dwayne L. Bentley; Yonggang Ji

(57) ABSTRACT

The present invention relates to a gel sheet (1) for use in a spot picker device wherein said gel sheet is provide with reference marks (5'–5''') which can be used to determine if the gel sheet (1) has been deformed between the stages of scanning the gel sheet and picking spots out of the gel sheet (1). The present invention also relates to a method of picking spots using such a gel sheet (1) and reference marks for use with the method.

6 Claims, 3 Drawing Sheets

GEL SPOT PICKER

FIELD OF THE INVENTION

The present invention relates to sheets of gels and methods for picking up gel plugs from sheets of gel.

PRIOR ART

Many biochemical analytical methods, such as 2 dimensional electrophoresis, produce results in the form of sheets of gel upon which the analysed substances are grouped in spots. Further analyse of the substances can be made by cutting out and picking up the cylindrical plugs of gel containing the spots of substances of interest and transferring the plugs to other devices such as microtitre plates or test tubes for further analysis.

In an automated system for picking spots of interest the gel can be treated with a coloured dye which can be absorbed by the substances of interest in order to make then visible. The sheet of gel can then be scanned and the results of the scanning analysed by a computer program, which calculates the co-ordinates of the spots. The gel can then be moved to a spot picking device called a spot picker and the co-ordinates of the spots of interest can be loaded into the computer which controls the spot picker. The computer controls the movement of the spot-picker's spot-picking bead and directs it to move to the co-ordinates of each spot that is to be picked up. The plugs of gel containing the spots are extracted from the sheet of gel by lowering a cylindrical hollow needle on the spot-picker head through the liquid covering the gel and the gel until it reaches the supporting base plate, applying a suction to the upper end of the needle in order to lift the plug off the base plate and into the needle where it is caught by a pieced bulkhead near the tip of the needle. The plug can then be transported by the spot picker head to a position above a well in a micro-titre plate or a test tube and then ejected out of the needle by pressurised liquid applied to the upper part of the needle. The spot can then be destained. In order to be sure that the correct material is extracted from the sheet of gel the spot picker head should be positioned to an accuracy of 0.1 mm or better.

A problem with this method is that it requires complex and expensive mechanical high precision guides for both the scanner and spot picker. Furthermore the geometry of the gel can change during transport between the scanner and the spot picker. This means that the spots move to new co-ordinates and leads to incorrect plugs of gel being picked. Additionally the individual destaining of the spots after they have been lifted out of the gel is time-consuming. The present invention aims to overcome these problems.

SUMMARY OF THE INVENTION

The present invention solves the problems of prior art devices by means of a gel sheet having the features in the characterising part of claim 1. A method in accordance with the present invention has the features presented in the characterising part of claim 6. Reference marks for use with the gel and method have the features presented in the characterising part of claim 7. A system for performing the method has the features mentioned in claim 10.

By means of the present invention, simplified guides for the scanner and spot picker may be used, or the use of guides and mounting fixtures can be eliminated, thus reducing the cost of the equipment and speeding up handling of gels. Additionally, spots can be extracted even if the geometry of the gel changes between being scanned and spot picking. Furthermore in embodiments of devices in accordance with the present invention it is possible to extract spots even after they have been destained.

DETAILED DESCRIPTION OF EMBODIMENTS ILLUSTRATING THE INVENTION

Figure 1:
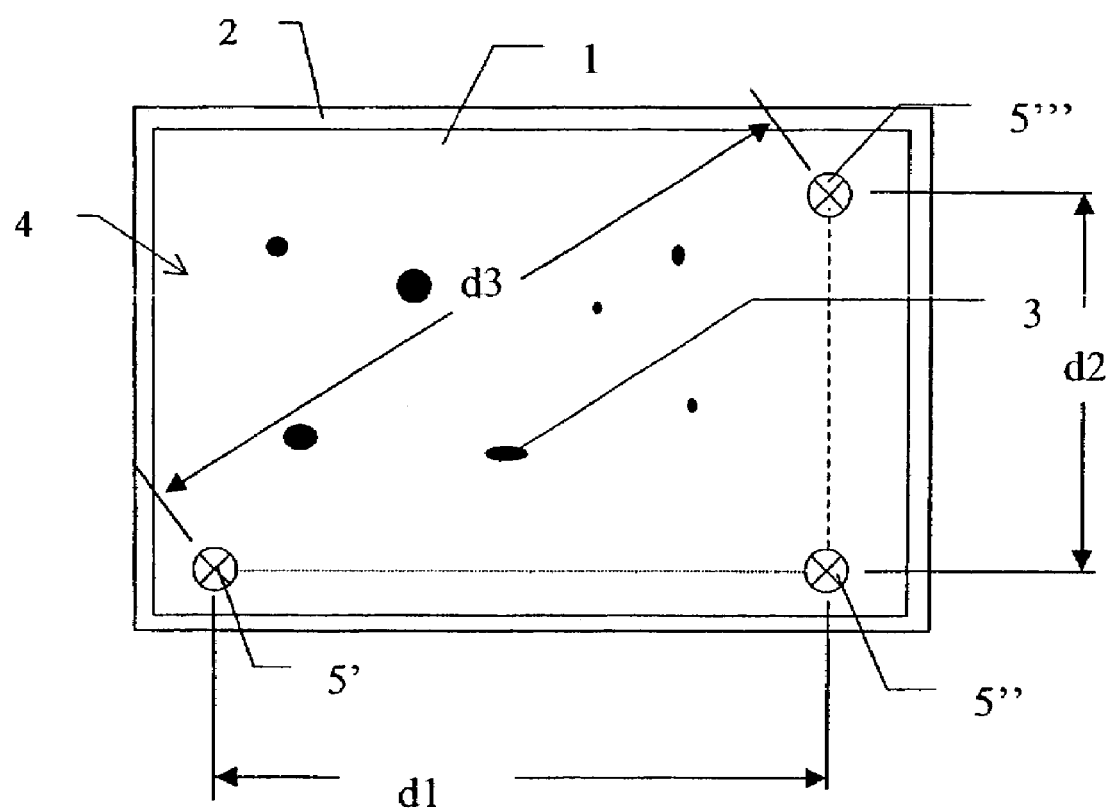
FIG. 1 shows schematically a view from above of an embodiment of a sheet of gel in accordance with the present invention.
Figure 2:
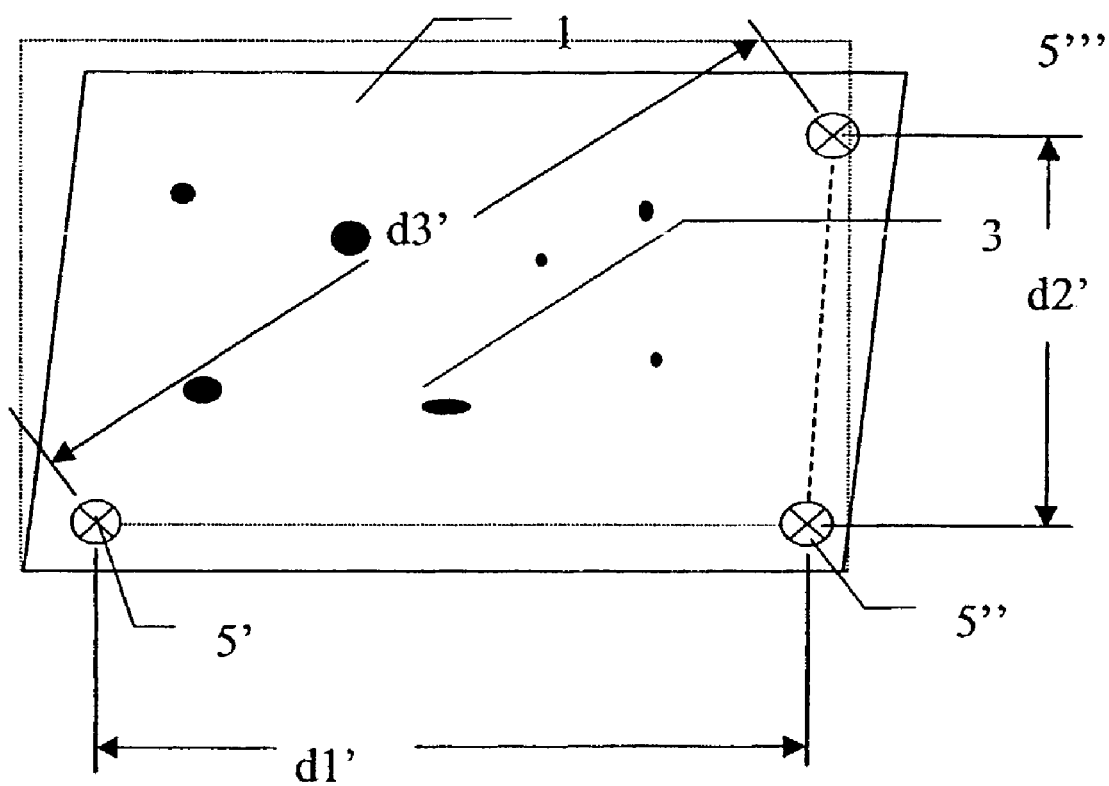
FIG. 2 shows the sheet of gel of FIG. 1 after it has been deformed.
Figure 3:
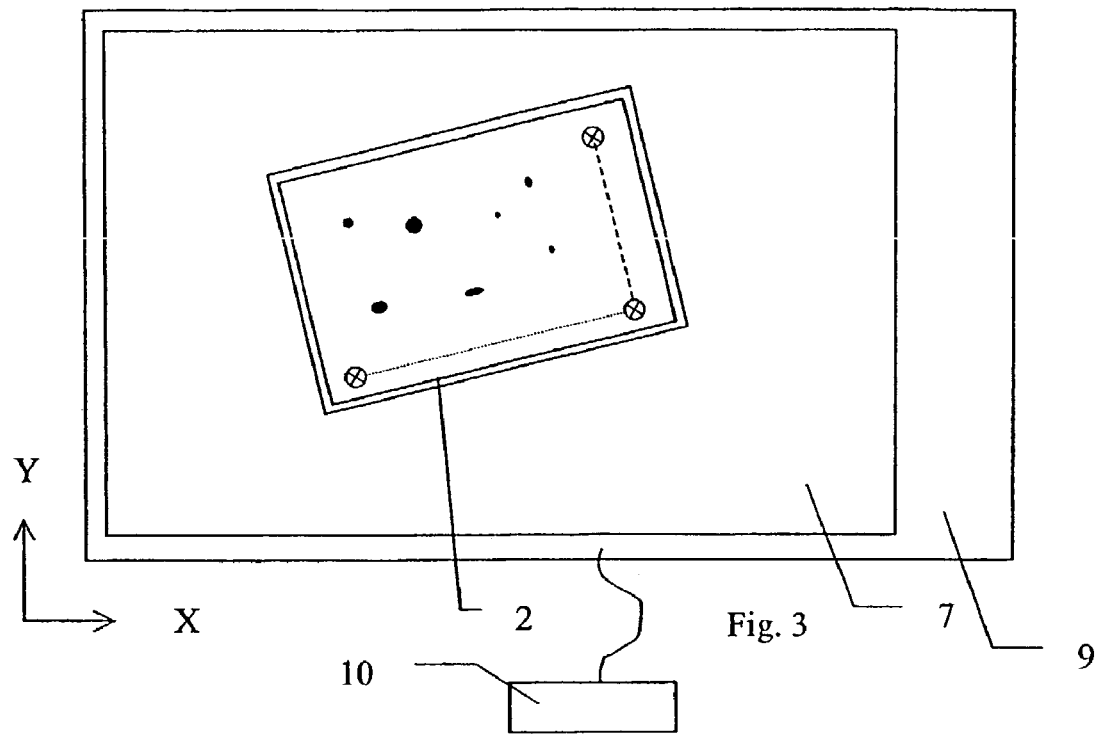
FIG. 3 shows an embodiment of a gel scanner in accordance with the present invention.
Figure 4:
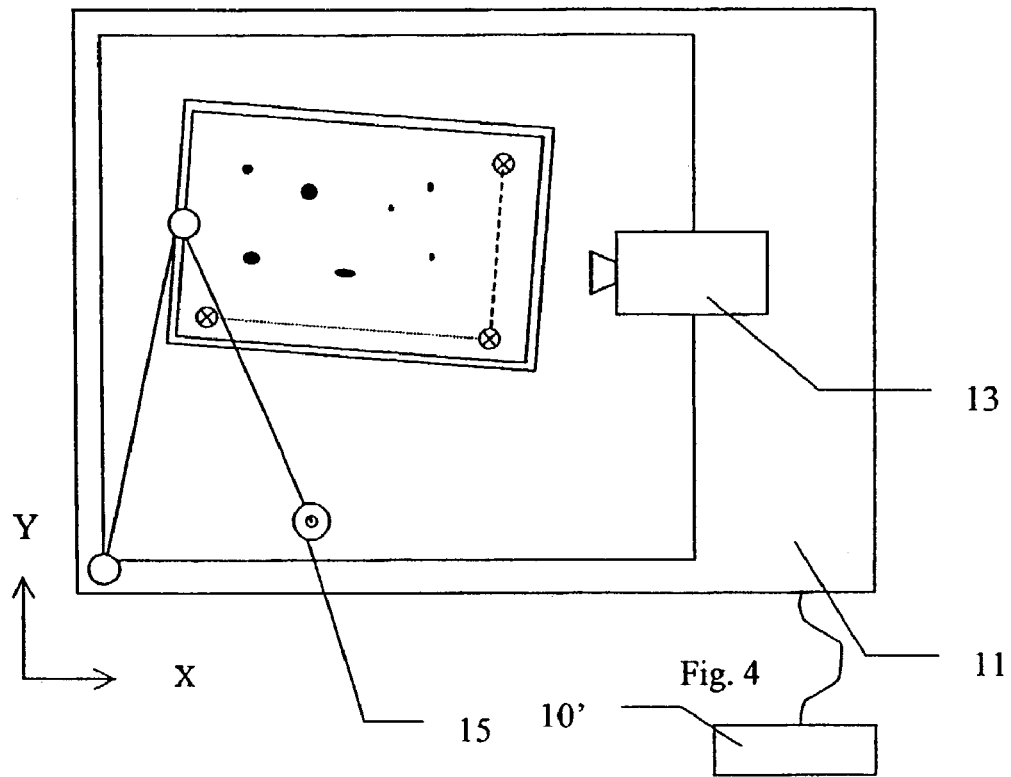
FIG. 4 shows an embodiment of a gel picker in accordance with the present invention.

FIG. 1 shows a view from above of a sheet of gel 1 in accordance with the present invention. Gel sheet 1 can, for example, be a sheet of gel in a frame 2 which has been to used in 2D electrophoresis and which has been subsequently stained in order to make the electrophoresed constituents of samples visible to a scanner, or a sheet of gel containing proteins that have been labelled with a dye prior to electrophoresis. These constituents of samples appear as spots 3 and in order to analysis them it is necessary to remove the plugs of gel containing the spots 3 from the sheet of gel. This is done by scanning the gel sheet 1 on the bed 7 of a scanner 9 as shown in FIG. 3 and recording in a storage means such as a computer memory in a control device 10 the positions of the spots 3 identified by the scanner 9. These stored positions can then be used later by the control device of a spot picker device. In the present invention, before the scanning is performed, the sheet of gel 1 is provided with reference marks 5'–5'" which are printed or painted or stuck or applied in any other suitable way onto the surface of the gel or into the gel or onto a surface under the gel, so that they are visible and detectable by the scanner. These reference marks 5'–5'" follow any deformation of the sheet of gel. When the gel is scanned the imaging software associated with control device 10 of the scanner 9 relates the co-ordinates of the spots to the reference marks and the distances (d1, d2, d3) between the reference marks is also measured. In other words, the position of each spot can be correlated to the position of the reference marks 5'–5'". For example, the imaging software can consider that an imaginary line joining reference mark 5' to reference mark 5" represents a base line in the Y-axis (shown by a dotted line) and a line joining reference mark 5" to reference mark 5'" represents a base line in the X-axis (shown by a dashed line). Thus the position of each spot 3 can be related to each base line and stored in memory. If desired the entire gel can now be destained. The gel and the information relating to the positions of the spots stored in the control device 10 can then be transferred to a spot picker device 11 (see FIG. 4) that is provided with a camera 13. The camera 13 is used with imaging software in the spot picker control device 10' to identify the reference marks 5'–5'" and to measure the distances (d1', d2', d3') between them. If the distances (d1', d2', d3') between them are the same as those distances (d1, d2, d3) measured by the scanner and stored in its memory then it can be assumed that the gel sheet 1 has not been deformed and a movable spot picker head 15 can be used to pick up the spots at the positions stored in the memory in the spot picker control device 10'. In order to provide an integrated system control device 10 and control device 10' preferably are the same device. If however, as shown in FIG. 2, the gel sheet has been deformed then some or all of the distances (d1', d2', d3') will be different from the stored distances (d1, d2, d3). This means that the spots 3 will no longer be at the positions stored in the memory. The spot picker device is provided with software that can make a correlation between the old and new positions of the reference markers 5'–5''' and then calculate a new position for each spot. For example, if the software calculates that the gel has been skewed 5% in both the X- and Y-directions then it can recalculate new positions for each spot 3 that are also skewed 5%. These new positions can then be used to guide the spot picker head to the spots even if the spots have been destained and are no longer visible. Additionally if after being transferred from the scanner 9 to the spot picker 11 the orientation of frame 2 with respect to the X-axis and Y-axis of the spot picker 11 is different to its orientation with respect to the X-axis and Y-axis of the scanner, it is possible for the spot picker software to identify the reference markers 5'–5''' in the images from the camera 13 and to calculate the positions of the spots in relation to these reference marks 5'–5'''. This means that no time or fixtures are required to align the frames 2 with the axes of the scanner or spot picker as the software can compensate for any misalignment.

While the invention has been illustrated by an embodiment using three reference marks it is of course possible to use more reference marks in order to more accurately identify how the gel has been deformed. In order to obtain the best results, at least one of the reference marks must be situated to one side of a straight line joining two of the other reference marks in order to provide a two-dimensional frame of reference.

However, if the gel is in the form of a long thin strip then it is possible to use only two longitudinally separated reference marks if it can be assumed that any deformations in the narrow transverse axis of the gel are negligible. Similarly, if the gel is stuck to a backing so that it is substantially fixed, then only two reference marks are needed to establish a frame of reference.

Furthermore the reference marks are not limited to the shape shown in the figures but may be of any suitable shape e.g. squares, crosses, triangles, alphanumeric symbols etc.

Depending on the type of scanner and camera used, the reference marks may be coloured or made of fluorescent material which must still be visible after the gel has been treated with a destaining process. The reference marks may be in the form of labels that have been printed or painted on one side and have an adhesive on the other side to allow them to adhere to the gel or, if the gel is sufficiently transparent, to an underlying support. The reference may be coated with different dyes or colours depending on the wavelength(s) of light used to scan the gel and the scanning method. If visible light is used then the reference mark could comprise one or more pigment of contrasting colour e.g. white or black. If excitation UV light of a certain wavelength (e.g. 480 nm, 530 nm, 620 nm, etc.) is used to cause dyed spots of interest in the gel to fluoresce at another wavelength (e.g. 530 nm, 590 nm, 680 nm, etc.), then the reference mark can comprise a dye or the same dye used to dye the samples (e.g. Cy2, Cy3, Cy5, etc.) that fluoresces at the same wavelength. It is also conceivable that the reference mark can contain more than one dye or pigment. For example, a reference mark could be printed or painted with a mixture containing one or more of the following dyes or pigments: Cy2 dye, Cy3 dye, Cy5 dye, Sypro ruby/red dye, Sypro orange/tangerine dye, magenta pigment (e.g. SPL 21N/JST 18 from Radiant Colors), chartreuse pigment (e.g. SPL 17N/JST 10 from Radiant Colors) or the like. The pigments and dyes can be dissolved in a varnish (e.g. UVF00106 from Akzo Nobel) and then painted or printed onto labels to form reference marks. Some dyes are almost insoluble in varnish and in that case it is necessary to first dissolve them in another solvent, such as dimethylsupoxide (DMSO), which mixes very well with the varnish. Alternatively the dyes and pigments may be dissolved in different solvents and applied in sequence to form different layers on the labels. The relative proportions of the different dyes and pigments are preferably chosen so that during scanning the reference mark has substantially the same pixel intensity irrespective of which of the normal excitation light wavelengths is used. This would simplify the use of the same labels for any scanning wavelength and permit multiple scans on the same sample using different excitation wavelengths and using the same camera to record the results.

The present invention is not limited to the embodiments described above but many changes and modifications may be made without departing from the scope of the inventive concept as defined in the following claims.

The invention claimed is:

1. A method for picking spots (3) out of a gel sheet (1) containing a plurality of spots comprising:
   a) applying at least two reference marks (5'–5''') to said gel sheet (1);
   b) measuring the distances (d1–d3) between said reference marks (5'–5''') and the distances between each of said spots (3) and said reference marks (5'–5'''), and storing said distances in a memory;
   c) moving said gel sheet to a spot picker device;
   d) measuring in said spot picker device the distances (d1'–d3') between said reference marks (5'–5''');
   e) comparing the distances (d1'–d3') and (d1–d3) in order to calculated how much the gel sheet (1) has been deformed;
   f) calculating a new position for each spot (3) based on the deformation calculated in step e); and,
   g) positioning the spot picker head at, and picking spots (3) at, the new position for each spot calculated in step f).

2. The method of claim 1 further comprising the step of destaining said gel sheet (1) before performing step g).

3. The method of claim 1 wherein said reference marks include at least one layer containing one or more dyes and/or pigments.

4. The method of claim 3 wherein said dye or dyes are selected from the group consisting of Cy2 dye, Cy3 dye, Cy5 dye, Sypro ruby/red dye, Sypro orange/tangerine dye and combinations thereof.

5. The method of claim 3 wherein the reference marks include an adhesive to allow the reference marks to adhere to the gel sheet.

6. A system for picking spots from a gel comprising a gel scanner (9), a spot picker device (11) including imaging means (13) and a spot picker (15), and control devices (10, 10') comprising software for correlating the position of reference marks (5'–5''') on an image of a gel scanned by said scanner (9) and the images of the same reference marks on the image of said gel produced by said imaging means (13).

* * * * *